United States Patent
Framroze

(10) Patent No.: US 10,328,090 B2
(45) Date of Patent: Jun. 25, 2019

(54) HONOKIOL AND MAGNOLOL FORMULATIONS WITH INCREASED STABILITY AND IMPROVED UPTAKE, AND METHODS OF USE THEREOF

(71) Applicant: ST IP Holding AG, Zug (CH)

(72) Inventor: Bomi P. Framroze, Mumbai (IN)

(73) Assignee: ST IP Holding AG, Zug (CH)

( * ) Notice: Subject to any disclaimer, the term of this patent is extended or adjusted under 35 U.S.C. 154(b) by 0 days.

(21) Appl. No.: 15/319,887

(22) PCT Filed: Jan. 18, 2016

(86) PCT No.: PCT/IN2016/050021
§ 371 (c)(1),
(2) Date: Dec. 19, 2016

(87) PCT Pub. No.: WO2017/029683
PCT Pub. Date: Feb. 23, 2017

(65) Prior Publication Data
US 2018/0147220 A1    May 31, 2018

(30) Foreign Application Priority Data
Aug. 17, 2015 (IN) .......................... 2534/DEL/2015

(51) Int. Cl.
| | | |
|---|---|---|
| A61K 31/685 | (2006.01) | |
| A61K 36/575 | (2006.01) | |
| A61K 35/00 | (2006.01) | |
| A61P 25/20 | (2006.01) | |
| A61P 25/28 | (2006.01) | |
| A61K 9/00 | (2006.01) | |
| C07F 5/02 | (2006.01) | |
| A61K 35/60 | (2006.01) | |

(52) U.S. Cl.
CPC .......... *A61K 31/685* (2013.01); *A61K 9/0056* (2013.01); *A61K 35/00* (2013.01); *A61K 35/60* (2013.01); *A61K 36/575* (2013.01); *A61P 25/20* (2018.01); *A61P 25/28* (2018.01); *C07F 5/02* (2013.01); *A61K 2300/00* (2013.01)

(58) Field of Classification Search
CPC .... A61K 31/355; A61K 31/685; A61K 35/60; A61K 9/0056; A61F 31/685; A61P 25/28
See application file for complete search history.

(56) References Cited

U.S. PATENT DOCUMENTS

| | | | |
|---|---|---|---|
| 6,582,735 B2 | 6/2003 | Stogniew et al. | |
| 6,814,987 B2 | 11/2004 | Stogniew et al. | |
| 7,347,985 B2 | 3/2008 | Maxwell et al. | |
| 7,470,442 B2 | 12/2008 | Dodds et al. | |
| 7,544,377 B2 | 6/2009 | Dodds et al. | |
| 7,592,025 B2 | 9/2009 | Dodds et al. | |
| 7,632,525 B2 | 12/2009 | Dodds et al. | |
| 7,744,932 B2 | 6/2010 | Faller et al. | |
| 8,012,514 B2 | 9/2011 | Maxwell et al. | |
| 8,084,066 B2 | 12/2011 | Faller et al. | |
| 8,163,304 B2 | 4/2012 | Dodds et al. | |
| 8,445,036 B2 | 5/2013 | Faller et al. | |
| 8,758,839 B2 | 6/2014 | Faller et al. | |
| 2013/0096087 A1 | 4/2013 | Van Der Beek et al. | |
| 2013/0230503 A1* | 9/2013 | Homberg ............... | A61K 31/20 424/94.1 |

FOREIGN PATENT DOCUMENTS

| | | | |
|---|---|---|---|
| WO | 2012-095731 A1 * | 7/2012 | |
| WO | 2012095731 * | 7/2012 | |
| WO | WO-2012/095731 A1 | 7/2012 | |
| WO | 2013/043151 A1 * | 3/2013 | |
| WO | 2013043157 * | 3/2013 | |
| WO | WO-2013/043151 A1 | 3/2013 | |
| WO | 2013/0230503 A1 * | 9/2013 | |

OTHER PUBLICATIONS

International Search Report and Written Opinion for International Application No. PCT/IN16/50021 dated Jul. 1, 2016.

* cited by examiner

*Primary Examiner* — Carlos A Azpuru
(74) *Attorney, Agent, or Firm* — Foley Hoag LLP

(57) ABSTRACT

Described herein are formulations and methods for treating, managing, or preventing sleeplessness or restlessness, for increasing focus or concentration, or for decreasing anxiety. The formulations comprise honokiol and magnolol, which are present in magnolia bark extract, in admixture with one or more polyunsaturated fatty acids, such as those found in virgin salmon oil. As compared to other lipid formulations of honokiol and magnolol, the formulations show improved stability and increased uptake.

20 Claims, No Drawings

HONOKIOL AND MAGNOLOL FORMULATIONS WITH INCREASED STABILITY AND IMPROVED UPTAKE, AND METHODS OF USE THEREOF

RELATED APPLICATIONS

This application is the United States National Stage application of PCT/IN16/050021, filed Jan. 18, 2016, which claims the benefit of priority to Indian Provisional Patent Application serial number 2534/DEL/2015, filed Aug. 17, 2015, the contents of both of which are hereby incorporated by reference.

BACKGROUND

Honokiol and magnolol (pictured below) are lignans isolated from the bark of trees belonging to the genus *Magnolia*.

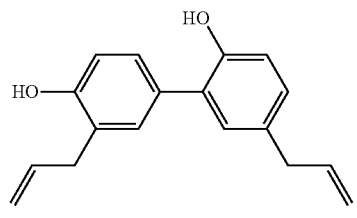

honokiol

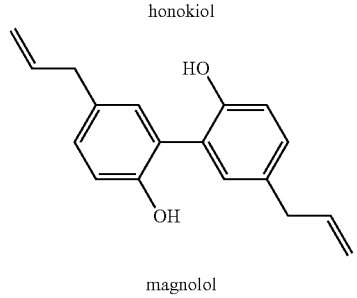

magnolol

Because of their physical properties, these compounds can readily cross the blood brain barrier and the blood-cerebrospinal fluid barrier. As a result, pharmaceutical formulations containing these active agents are potentially potent therapies with high bioavailability. Indeed, traditional eastern herbal medicines known to contain these compounds have a variety of uses, and modern medicine also indicates that the compounds have antitumorgenic and neurotrophic properties.

For example, honokiol and magnolol have been described as modulators of cortisol production and are associated with improved sleep and weight loss. The mechanism of honokiol and magnolol intestinal absorption is largely unknown. Similar polarity small molecules have been proposed to be absorbed via an active transport protein in the small intestine. However, because of their highly lipophilic nature, uptake from currently available oral formulations can prove problematic.

There exists a need for improved oral formulations comprising honokiol and magnolol that have good shelf-life and improved uptake upon administration.

SUMMARY

In certain embodiments, the invention relates to a formulation comprising, consisting essentially of, or consisting of virgin salmon oil, honokiol, and magnolol.

In certain embodiments, the invention relates to a formulation comprising, consisting essentially of, or consisting of virgin salmon oil, honokiol, magnolol, and vitamin A.

In certain embodiments, the invention relates to a formulation comprising, consisting essentially of, or consisting of virgin salmon oil, honokiol, magnolol, vitamin A, and phosphatidylserine.

In certain embodiments, the invention relates to a formulation comprising, consisting essentially of, or consisting of virgin salmon oil, honokiol, magnolol, vitamin A, phosphatidylserine, and hydroxytyrosol.

In certain embodiments, the invention relates to a formulation comprising, consisting essentially of, or consisting of virgin salmon oil, honokiol, magnolol, vitamin A, phosphatidylserine, olive oil, and hydroxytyrosol.

In certain embodiments, the invention relates to an oral dosage form comprising any of the formulations described herein.

In certain embodiments, the invention relates to a method of treating, managing, or preventing sleeplessness or restlessness, increasing focus or concentration, or decreasing anxiety, comprising administering to a subject in need thereof an effective amount of any of the formulations described herein, or any of the oral dosage forms described herein.

DETAILED DESCRIPTION

Definitions

The term "effective amount" as used herein refers to the amount necessary to elicit the desired biological response. As will be appreciated by those of ordinary skill in this art, the effective amount of a drug may vary depending on such factors as the desired biological endpoint, the drug to be delivered, the composition of any additional active or inactive ingredients, the target tissue, etc.

As used herein, the term "extract" refers to a product prepared by extraction. The extract may be in the form of a solution in a solvent, or the extract may be a concentrate or essence which is free of, or substantially free of solvent. The extract also may be formulated into a pharmaceutical composition or food product, as described further below. The term extract may be a single extract obtained from a particular extraction step or series of extraction steps or the extract also may be a combination of extracts obtained from separate extraction steps or separate feedstocks. Such combined extracts are thus also encompassed by the term "extract."

As used herein, "feedstock" generally refers to raw plant material, comprising whole plants alone, or in combination with one or more constituent parts of a plant comprising leaves, roots, including, but not limited to, main roots, tail roots, and fiber roots, stems, bark, leaves, berries, seeds, and flowers, wherein the plant or constituent parts may comprise material that is raw, dried, steamed, heated or otherwise subjected to physical processing to facilitate processing, which may further comprise material that is intact, chopped, diced, milled, ground or otherwise processed to affected the size and physical integrity of the plant material. Occasionally, the term "feedstock" may be used to characterize an extraction product that is to be used as feed source for additional extraction processes.

As used herein, the term "fraction" means the extraction composition comprising a specific group of chemical compounds characterized by certain physical, chemical properties or physical or chemical properties.

A "patient," "subject" or "host" to be treated by the subject method may mean either a human or non-human animal.

The term "pharmaceutically-acceptable salts" is art-recognized and refers to the relatively non-toxic, inorganic and organic acid addition salts of compounds, including, for example, those contained in compositions of the invention.

The term "preventing", when used in relation to a condition, is well understood in the art, and includes administration of a composition which reduces the frequency of, or delays the onset of, symptoms of a medical condition in a subject relative to a subject which does not receive the composition.

The term "prophylactic or therapeutic" treatment is art-recognized and includes administration to the host of one or more of the subject compositions. If it is administered prior to clinical manifestation of the unwanted condition (e.g., disease or other unwanted state of the host animal) then the treatment is prophylactic, i.e., it protects the host against developing the unwanted condition, whereas if it is administered after manifestation of the unwanted condition, the treatment is therapeutic (i.e., it is intended to diminish, ameliorate, or stabilize the existing unwanted condition or side effects thereof).

The term "synergistic" is art-recognized and refers to two or more components working together so that the total effect is greater than the sum of the components.

The term "treating" is art-recognized and refers to curing as well as ameliorating at least one symptom of any condition or disorder.

Exemplary Formulations

In certain embodiments, the invention relates to a formulation comprising, consisting essentially of, or consisting of a polyunsaturated fatty acid, honokiol, and magnolol.

In certain embodiments, the invention relates to a formulation comprising, consisting essentially of, or consisting of one or more polyunsaturated fatty acids, honokiol, and magnolol.

In certain embodiments, the invention relates to a formulation comprising, consisting essentially of, or consisting of one or more polyunsaturated fatty acids, honokiol, magnolol, and vitamin A.

In certain embodiments, the invention relates to a formulation comprising, consisting essentially of, or consisting of one or more polyunsaturated fatty acids, honokiol, magnolol, vitamin A, and phosphatidylserine.

In certain embodiments, the invention relates to a formulation comprising, consisting essentially of, or consisting of one or more polyunsaturated fatty acids, honokiol, magnolol, vitamin A, phosphatidylserine, and hydroxytyrosol.

In certain embodiments, the invention relates to a formulation comprising, consisting essentially of, or consisting of virgin salmon oil, honokiol, and magnolol.

In certain embodiments, the invention relates to a formulation comprising, consisting essentially of, or consisting of virgin salmon oil, honokiol, magnolol, and vitamin A.

In certain embodiments, the invention relates to a formulation comprising, consisting essentially of, or consisting of virgin salmon oil, honokiol, magnolol, vitamin A, and phosphatidylserine.

In certain embodiments, the invention relates to a formulation comprising, consisting essentially of, or consisting of virgin salmon oil, honokiol, magnolol, vitamin A, phosphatidylserine, and hydroxytyrosol.

In certain embodiments, the invention relates to a formulation comprising, consisting essentially of, or consisting of virgin salmon oil, honokiol, magnolol, vitamin A, phosphatidylserine, olive oil, and hydroxytyrosol.

In certain embodiments, the invention relates to any of the formulations described herein, wherein the concentration of PUFA in the VSO is from about 20% to about 40% by weight of VSO, for example, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, or about 40% by weight of VSO.

In certain embodiments, the invention relates to any of the formulations described herein, wherein the VSO comprises astaxanthin.

In certain embodiments, the invention relates to any of the formulations described herein, wherein the concentration of VSO in the formulation is from about 40% to about 90% by weight of the formulation, for example, about 45%, about 50%, about 55%, about 60%, about 65%, about 70%, about 75%, about 80%, or about 85% by weight of the formulation, preferably about 75% by weight of the formulation.

In certain embodiments, the invention relates to any of the formulations described herein, wherein the concentration of honokiol in the formulation is from about 1% to about 10% by weight of the formulation, for example, about 1%, about 2%, about 3%, about 4%, about 5%, about 6%, about 7%, about 8%, about 9%, or about 10% by weight of the formulation, preferably about 2% by weight of the formulation.

In certain embodiments, the invention relates to any of the formulations described herein, wherein the concentration of magnolol in the formulation is from about 1% to about 10% by weight of the formulation, for example, about 1%, about 2%, about 3%, about 4%, about 5%, about 6%, about 7%, about 8%, about 9%, or about 10% by weight of the formulation, preferably about 2% by weight of the formulation.

In certain embodiments, the invention relates to any of the formulations described herein, wherein the formulation comprises vitamin A; and the concentration of vitamin A in the formulation is from about 0.01% to about 1% by weight of the formulation, for example, about 0.01%, about 0.02%, about 0.03%, about 0.04%, about 0.05%, about 0.06%, about 0.07%, about 0.08%, about 0.09%, about 0.1%, about 0.2%, about 0.3%, about 0.4%, about 0.5%, about 0.6%, about 0.7%, about 0.8%, about 0.9%, or about 1% by weight of the formulation.

In certain embodiments, the invention relates to any of the formulations described herein, wherein the formulation comprises phosphatidylserine; and the concentration of phosphatidylserine in the formulation is from about 4% to about 20% by weight of the formulation, for example, about 4%, about 5%, about 6%, about 7%, about 8%, about 9%, about 10%, about 11%, or about 12% by weight of the formulation, preferably about 7% by weight of the formulation.

In certain embodiments, the invention relates to any of the formulations described herein, wherein the formulation comprises olive oil; and the concentration of olive oil in the formulation is from about 5% to about 15% by weight of the formulation, for example, about 5%, about 6%, about 7%, about 8%, about 9%, about 10%, about 11%, about 12%, about 13%, about 14%, or about 15% by weight of the formulation, preferably about 11% by weight of the formulation. In alternative embodiments, the invention relates to any of the formulations described herein, wherein the formulation does not comprise olive oil.

In certain embodiments, the invention relates to any of the formulations described herein, wherein the formulation does not comprise lecithin.

In certain embodiments, the invention relates to any of the formulations described herein, wherein honokiol is from magnolia bark extract.

In certain embodiments, the invention relates to any of the formulations described herein, wherein magnolol is from magnolia bark extract.

In certain embodiments, the invention relates to any of the formulations described herein, wherein the pH of the formulation is from about 6 to about 8. In certain embodiments, the invention relates to any of the formulations described herein, wherein the pH of the formulation is about 6.0, about 6.5, about 7.0, about 7.5, or about 8.0.

In certain embodiments, the invention relates to any of the formulations described herein, wherein less than about 18%, less than about 17%, less than about 16%, less than about 15%, less than about 14%, less than about 13%, less than about 12%, less than about 11%, less than about 10%, less than about 9%, less than about 8%, or less than about 7% of the honokiol or the magnolol present in the formulation at day 0 decomposes upon storage of the formulation at about 54° C. and about 75% relative humidity for a period of 21 d. While not wishing to be bound by any particular theory, in general, oils containing polyunsaturated fatty acids (PUFA) are much less stable than oils containing saturated fatty acids (SFA). However, Tables 1-4 indicate that honokiol and magnolol are stabilized by oils containing a particular concentration or number of unsaturations (compare VSO with coconut oil, for example).

In certain embodiments, the invention relates to any of the formulations described herein, wherein more than about 11%, more than about 12%, or more than about 13% of the honokiol or the magnolol present in the formulation in the apical layer at time 0 is absorbed into the basal layer after 2 h. While not wishing to be bound by any particular theory, the formulations have improved cellular uptake as compared to aqueous formulations comprising honokiol and magnolol or lecithin-containing formulations comprising honokiol and magnolol.

In certain embodiments, the invention relates to any of the formulations described herein, wherein the formulation is in the form of an oral dosage form.

In certain embodiments, the invention relates to any of the formulations described herein, wherein the oral dosage form is a soft gel capsule.

In certain embodiments, the invention relates to a soft gel capsule comprising, consisting essentially of, or consisting of any of the formulations described herein.

In certain embodiments, the invention relates to any one of the formulations described herein, which is formulated as a pharmaceutical formulation, a nutraceutial formulation, a functional food, or a dietary supplement.

In certain embodiments, the invention relates to any formulation described herein in forms such as a paste, powder, oils, liquids, suspensions, solutions, or other forms, comprising, one or more fractions or sub-fractions to be used as dietary supplements, nutraceuticals, or such other preparations that may be used to prevent or treat various human ailments. The formulations can be processed to produce such consumable items, for example, by mixing them into a food product, in a capsule or tablet, or providing the paste itself for use as a dietary supplement, with sweeteners or flavors added as appropriate. Accordingly, such formulations may include, but are not limited to, formulations for oral delivery in the form of tablets, capsules (such as soft gel capsules), lozenges, liquids, emulsions, dry flowable powders and rapid dissolve tablets. The magnitude of the dietary dose of an active ingredient in the acute or chronic management of a disorder or condition will vary with the severity of the disorder or condition to be treated and the route of administration. The dose, and perhaps the dose frequency, will also vary according to age, body weight, response, and the past medical history of the consumer or subject. Suitable dosing regimens can be readily selected by those skilled in the art with due consideration of such factors. For example, subjects would be expected to benefit from daily dosages in the range of from about 50 mg to about 1000 mg. For example, a soft gel capsule comprising about 50, 55, 60, 65, 70, 75, 80, 85, 90, 95, 100, 105, 110, 115, 120, 125, 130, 135, 140, 145 or 150 mg of the extract can be administered once or twice a day to a subject.

Formulations can be in the form of a paste, resin, oil, powder or liquid. Liquid formulations for oral administration may take the form of, for example, solutions, syrups or suspensions, or they may be presented as a dry product for reconstitution with water or other suitable vehicle prior to administration. Such liquid formulations may be prepared by conventional means with pharmaceutically acceptable additives such as suspending agents (e.g., sorbitol syrup, methyl cellulose, or hydrogenated edible fats); emulsifying agents (e.g., lecithin or acacia); non-aqueous vehicles (e.g., almond oil, oily esters or ethyl alcohol); preservatives (e.g., methyl or propyl p-hydroxybenzoates or sorbic acid); and artificial or natural colors or sweeteners. Liquid formulations can be administered to humans or animals in pharmaceutical carriers known to those skilled in the art. Such pharmaceutical carriers include, but are not limited to, capsules, lozenges, syrups, sprays, rinses, and mouthwash.

The formulations may comprise extracts from other plants such as, but not limited to, varieties of Gymnemia, turmeric, boswellia, guarana, cherry, lettuce, Echinacia, piper betel leaf, *Areca catechu*, muira puama, ginger, willow, suma, kava, horny goat weed, *Ginkgo biloba*, mate, garlic, puncture vine, arctic root *astragalus, eucommia, gastropodia*, and *uncaria*, or pharmaceutical or nutraceutical agents.

It will be recognized that dietary supplements may not use the same formulation ingredients or have the same sterile and other FDA requirements as pharmaceutical compositions. The dietary supplements may be in liquid form, for example, solutions, syrups or suspensions, or may be in the form of a product for reconstitution with water or any other suitable liquid before use. Such liquid preparations may be prepared by conventional means such as a tea, health beverage, dietary shake, liquid concentrate, or liquid soluble tablet, capsule, pill, or powder such that the beverage may be prepared by dissolving the liquid soluble tablet, capsule, pill, or powder within a liquid and consuming the resulting beverage. Alternatively, the dietary supplements may take the form of tablets or capsules, such as soft gel capsules, prepared by conventional means and optionally including other dietary supplements including vitamins, minerals, other herbal supplements, binding agents, fillers, lubricants, disintegrants, or wetting agents, as those discussed above. The tablets may be coated by methods well-known in the art.

Exemplary Methods of Treatment and Prevention

In certain embodiments, the invention relates to a method of treating, managing, or preventing sleeplessness or restlessness, increasing focus or concentration, or decreasing anxiety, comprising administering to a subject in need thereof an effective amount of any one of the formulations described herein. In certain embodiments, methods are described in PCT application publication no. WO 2012/095731, which is hereby incorporated by reference in its entirety.

In certain embodiments, the invention relates to any of the methods described herein, wherein the subject is a mammal, for example, a human.

As used herein, unless otherwise specified, the term "treating sleeplessness" or "treatment of sleeplessness" includes, but is not limited to, preventing or reducing the disturbances in falling asleep, staying asleep, duration of sleep, or abnormal sleep behaviors.

As used herein, unless otherwise specified, the term "treating restlessness", "treatment of restlessness" or "preventing restlessness" includes, but is not limited to, causing to rest or relax preferably without inducing sedation or hypnosis, inducing relaxation without inducing muscle relaxation, and relieving nervous tension or stress. Thus, the invention also encompasses methods of inducing relaxation without reduction or loss of motor function in humans.

In certain embodiments, the invention relates to any of the methods described herein, wherein the formulation is administered in an amount sufficient to prevent the onset of sleeplessness or sleeplessness related symptoms. In another embodiment, for subjects already suffering from sleeplessness, the formulation is administered in an amount sufficient to reduce sleeplessness or the symptoms associated with sleeplessness, or in an amount sufficient to treat sleeplessness or the symptoms associated with sleeplessness.

In certain embodiments, the invention relates to any of the methods described herein, wherein the formulation is administered in an amount sufficient to prevent the onset of restlessness or restlessness related symptoms. In certain embodiments, the invention relates to any of the methods described herein, wherein the formulation is administered in an amount and at a regular interval sufficient to reduce or eliminate restlessness related symptoms in mammals suffering from restlessness. In certain embodiments, the invention relates to any of the methods described herein, wherein the formulation is administered in a therapeutically sufficient amount to either prevent or treat restlessness.

In certain embodiments, the invention relates to any of the methods described herein, wherein the formulation induces relaxation without loss of motor function and restful sleep. Without being limited by theory, it is believed that honokiol and magnolol act synergistically or at least more than additively by binding to one or more receptor sites to collectively diminish the symptoms of sleeplessness or restlessness without causing a sedative or addictive effect.

In certain embodiments, the invention relates to a method of treating a variety of disorders of the central nervous system (CNS).

In certain embodiments, the invention relates to a method of increasing focus or concentration in a subject suffering from an attention deficit disorder (ADD). ADDs are characterized by hyperactive, impulsive or inattentive symptoms that cause impairment in social, academic, or occupational functioning, and are often present in two or more settings, school (or work) and at home, for example. For the Inattentive Type, at least 6 of the following symptoms have persisted for at least 6 months: lack of attention to details/careless mistakes; lack of sustained attention; poor listener; failure to follow through on tasks; poor organization; avoids tasks requiring sustained mental effort; loses things; easily distracted; and forgetful. For the Hyperactive-Impulsive Type, at least 6 of the following symptoms have persisted for at least 6 months: fidgeting/squirming; leaving seat; inappropriate running/climbing; difficulty with quiet activities; "on the go"; excessive talking; blurting answers; can't wait turn, and intrusive behavior. The combined type includes both inattentive and hyperactive-impulsive behaviors.

In certain embodiments, the invention relates to a method of decreasing anxiety that is a result of an anxiety disorder, such as panic disorder with or without agoraphobia, agoraphobia without history of panic disorder, animal and other phobias including social phobias, obsessive-compulsive disorder, stress disorders including post-traumatic and acute stress disorder, and generalized or substance-induced anxiety disorder; neuroses; convulsions; migraine; depressive or bipolar disorders, for example single-episode or recurrent major depressive disorder, dysthymic disorder, bipolar I and bipolar II manic disorders, and cyclothymic disorder; psychotic disorders including schizophrenia; neurodegeneration arising from cerebral ischemia; attention deficit hyperactivity disorder; Tourette's syndrome; speech disorders, including stuttering; and disorders of circadian rhythm, e.g. in subjects suffering from the effects of jet lag or shift work.

In certain embodiments, the invention relates to any of the methods described herein, wherein administering the formulation reduces or avoids adverse effects associated with certain CNS drugs such as physical dependency, withdrawal problems, impaired coordination, loss or reduction of motor function, slowed reaction time, sedation, weight gain, constipation, dry mouth, confusion, blurred vision, nausea, diarrhea, or headaches.

In certain embodiments, the invention relates to any of the methods described herein, wherein the formulation is co-administered with other known therapeutic agents or techniques for treating, managing, or preventing sleeplessness or restlessness, increasing focus or concentration, or decreasing anxiety. Such agents may include vitamins and minerals, such as magnesium, calcium, or non-sedating sleep aids.

EXEMPLIFICATION

The invention is further illustrated by the following Examples which should not be construed as limiting in any way. The Examples and discoveries described herein are representative. As such, the studies and results described in the Examples section herein may be used as a guideline.

Example 1

Stability of Fatty-acid Formulations Comprising Honokiol and Magnolol

Formulations comprising honokiol and magnolol in various fatty acid media were prepared.

i. Coconut Oil formulation
  10 mg Honokiol
  10 mg Magnolol
  50 mg phosphatidylserine 70%
  50 mg olive oil (hydroxytyrosol supplemented to between 450-500 umol/kg oil)
  0.5 mg Vit A (as betacarotene)
  350 mg Coconut Oil ii. Avocado Oil formulation
  10 mg Honokiol
  10 mg Magnolol
  50 mg phosphatidylserine 70%
  50 mg olive oil (hydroxytyrosol supplemented to between 450-500 umol/kg oil)
  0.5 mg Vit A (as betacarotene)
  350 mg Avocado Oil iii. Virgin Salmon Oil formulation
 10 mg Honokiol
 10 mg Magnolol
 50 mg phosphatidylserine 70%
 50 mg olive oil (hydroxytyrosol supplemented to between 450-500 umol/kg oil)
 0.5mg Vit A (as betacarotene)
 350 mg Virgin Salmon Oil
iv. Lecithin formulation
 10 mg Honokiol
 10 mg Magnolol
 50 mg phosphatidylserine 70%
 50 mg olive oil (hydroxytyrosol supplemented to between 450-500 umol/kg oil)
 0.5 mg Vit A (as betacarotene)
 350 mg lecithin from soybeans
v. Fish Oil Formulation
 10 mg Honokiol
 10 mg Magnolol
 50 mg phosphatidylserine 70%
 50 mg olive oil (hydroxytyrosol supplemented to between 450-500 umol/kg oil)
 0.5 mg Vit A (as betacarotene)
 350 mg Fish Oil

TABLE 1

Description of fatty acids in various formulations

| Formulation | Fatty acids |
| --- | --- |
| Coconut Oil | High SFA |
| Avocado Oil (AO) | High MUFA |
| Virgin Salmon Oil (VSO) | Mod PUFA |
| Lecithin | |
| Fish Oil (FO) | High PUFA |

The main difference between FO and VSO is that FO undergoes multistep processing—bleaching to decolor/deodorize with caustic solution, acid hydrolysis to free fatty acids, distillation, and re-esterfication to methyl/ethyl esters. As a result, FO is concentrated for only two PUFAs: eicosapentaenoic acid (EPA) and docosahexaenoic acid (DHA). On the other hand, VSO is not processed at all and hence has the natural full range of PUFA in natural concentrations. Also present in VSO are natural antioxidants like astaxanthin, which are destroyed during FO processing. The components of FO and VSO are described in Table 2.

TABLE 2

Components of FO and VSO

| | FO | VSO |
| --- | --- | --- |
| % Triglyceride | 0 | 99 |
| % Methyl Ester | 93 | 0 |
| % Free Fatty Acid | 4.8 | <0.5 |
| Saturated Fatty Acid (mg/dg) | 20 | 15 |
| Mono Unsaturated Fatty Acid (mg/dg) | 30 | 55 |
| Poly Unsaturated Fatty Acid (mg/dg) | 48 | 30 |
| EPA (mg/dg) | 18 | 5 |
| DHA (mg/dg) | 26 | 10 |
| DPA (mg/dg) | 0 | 4 |
| Omega-7's (mg/dg) | <1 | 4 |
| Omega-9's (mg/dg) | 2 | 5 |
| Astaxanthin (µg/g) | 0 | 8 |

The samples were stored at 54° C. and 75% relative humidity. Periodically, the concentration of both actives remaining in the formulation was determined by gas chromatography.

TABLE 3

% Honokiol over time

| Formulation | Day 0 | Day 7 | Day 14 | Day 21 |
| --- | --- | --- | --- | --- |
| Coconut Oil | 10.2 | 8.8 | 8.2 | 8.2 |
| AO | 10.1 | 9.1 | 8.4 | 7.7 |
| VSO | 10.4 | 10.1 | 9.9 | 9.7 |
| Lecithin | 10.2 | 9.5 | 8.7 | 7.9 |
| FO | 9.9 | 9.1 | 8.3 | 7.7 |

TABLE 4

% Magnolol over time

| Formulation | Day 0 | Day 7 | Day 14 | Day 21 |
| --- | --- | --- | --- | --- |
| Coconut Oil | 10.7 | 8.5 | 8.1 | 8.1 |
| AO | 10.3 | 9 | 8.4 | 8 |
| VSO | 10 | 9.8 | 9.7 | 9.6 |
| Lecithin | 10.1 | 9.5 | 8.4 | 8 |
| FO | 10.2 | 9.1 | 8.5 | 7.8 |

TABLE 5

Summary of active agent stability after 21 d

| Formulation | Avg % loss of both actives over 21 d |
| --- | --- |
| Coconut Oil | 22.0% |
| AO | 23.0% |
| VSO | 5.4% |
| Lecithin | 21.7% |
| FO | 22.9% |

Example 2

A Comparative Study on Uptake of Honokiol and Magnolol Between a Moderate Pufa Oil Formulation, Lecithin Oil Formulation, and Ph 4 Buffered Aqueous Formulation Using a Caco-2 In Vitro Cell Assay Aim The aim of this study is to use a Caco-2 uptake kit for measuring intestinal uptake of honokiol and magnolol (H&K) active ingredients from Magnolia Bark from an equimolar solution in a moderate PUFA oil emulsion, lecithin based emulsion and pH 4 buffered aqueous formulation.

Background

Intestinal cell cultures, like Caco-2 cell lines have gained in popularity as an in vitro model of intestinal absorption. The human colon carcinoma cell line, Caco-2, is grown on microporous membranes in bifurcated chambers and the cells differentiated spontaneously into bipolar enterocytes that exhibit many of the characteristics of normal epithelial cells (microvilli, tight intercellular junctions and border associated enzymes). The cells grow differentiated so that the apical pole extends into the upper chamber and the basal lateral pole is exposed to the lower chamber. The study can then measure H&K uptake from the apical chamber, transport into the cell and secretion into the basal chamber.

Two different oil matrix 1:1 emulsions at pH 7 were compared with a pH 4 buffered aqueous matrix. It should be noted that Magnolia Bark extracts are currently only available formulated as powders in two-piece capsules.

Methods

Assay Preparation

A commercial 24-well Caco-2 Cell Culture kit was directly used in this study.

Sample Preparation

1. H&K in moderate PUFA formulation was prepared by mixing 50 mg each of honokiol and magnolol in 10 mL VSO and sonicated to give 0.1% H&K test solution A.
2. H&K in lecithin formulation was prepared by mixing 50 mg each of honokiol and magnolol in 10 ml lecithin oil and sonicated to give 0.1% H&K test solution B.
3. H&K in aqueous buffer formulation was prepared by mixing 50 mg each of honokiol and magnolol in 10 ml of a pH 4 acetate buffered solution containing 0.5% Tween surfactant (SigmaAldrich Chemicals Inc.) and sonicated for 2 h to give 0.1% H&K test solution C.

Note: H&K stability in all 3 solutions was confirmed at the end of 4 h at 37° C. by area % GC to confirm formulation stability throughout the Caco-2 test protocol time.

Experiment Summary

1. Used two emulsions, 1:1 and 1:4 of the above test formulations A, B, C in HBSS.
2. Prepared 24-well Caco-2 plate as per normal protocols (250 μl in Apical chamber and 750 μl in Basal chamber). Repeated washing steps two times before step 3.
3. Filled the apical compartments of the Transwell plate in triplicate with 275 μl of test diluted 1:1 and 1:10 emulsions of A, B, C. The remaining 6 wells were treated with Lucifer yellow-CH dilutions as a marker for paracellular permeability and to confirm Caco-2 monolayer integrity through the assay.
4. Filled each of corresponding basal compartments of the Transwell plate with 750 μl of pre-warmed (37° C.) HBSS.
5. Recovered 25 μl from the apical compartments (Apical Time 0 h sample) and stored at 20° C. for analysis.
6. Transferred the apical integrated compartments of the Transwell plate onto the top of the basal compartments.
7. Incubated for 2 h.
8. Removed the plate from the incubator and split apical compartments from basal compartments in order to stop permeability assay.
9. Recovered 25 μl from the apical compartments (Apical Time 2 h sample) and stored at 20° C. for analysis.
10. Recovered 25 μl from the basal compartments (Basal Time 2 h samples) in Eppendorff tubes and stored at 20° C. until analysis.
11. Analyzed 2μl injection samples of each of the 3×18 apical and basal test compartment fractions for H&K quantification by GC area % analysis against standard.

Results and Discussion

This Caco-2 uptake trial was used to measure H+K uptake from three different formulations and the results are summarized below.

TABLE 6

Effect of 2 h exposure to H + K in test formulations A, B and C

| TREATMENT | Dilution | n | Apical 0 h H + K ug/well | SD | Apical 2 h H + K ug/well | SD | Basal 2 h H + K ug/well | SD |
|---|---|---|---|---|---|---|---|---|
| Formulation A | 1:1 | 3 | 10.26 | 0.065 | 8.68 | 0.053 | $1.38^a$ | 0.078 |
| Formulation A | 1:10 | 3 | 2.76 | 0.091 | 2.1 | 0.092 | 0.39 | 0.044 |
| Formulation B | 1:1 | 3 | 10.4 | 0.073 | 9.04 | 0.064 | $1.14^a$ | 0.059 |
| Formulation B | 1:10 | 3 | 2.44 | 0.084 | 1.9 | 0.057 | 0.28 | 0.063 |
| Formulation C | 1:1 | 3 | 10.08 | 0.061 | 9.82 | 0.086 | $0.22^b$ | 0.071 |
| Formulation C | 1:10 | 3 | 2.62 | 0.088 | 2.16 | 0.092 | 0.12 | 0.084 |

The results at the 1:1 dilution had a good mass balance between the apical and basal layers at the end of 2 h incubation using GC area % analysis. The results at 1:10 dilution tracked a similar trend for uptake but the mass balance was too poor to draw any relevant conclusions.

H+K in both the oil emulsion formulations A & B showed much better uptake as compared to the aqueous buffered formulation C (i.e., superscript a and superscript b are statistically different from each other).

Example 3

Exemplary Methods of Obtaining Extract Comprising Honokiol and Magnolol

The plant parts of the Magnoliaceae plant may be cut into small pieces or ground into a powder. Preferably, the plant part includes an extract of the Magnoliaceae plant. During a typical extraction process, the Magnoliaceae plant body, preferably cut into small pieces or ground into a powder, is placed in a Soxhlet extractor and extracted with any suitable solvent. Typical solvents include, but are not limited to, water, lower alcohols, or mixtures thereof. Preferably, the solvents used in the extraction include water, ethanol, and mixtures thereof. The solvent is maintained at reflux and the Magnoliaceae plant body is extracted for about 8 hours to about 48 hours. Preferably, the Magnoliaceae plant is extracted for about 12 hours to about 40 hours, and more preferably for about 18 hours to about 30 hours.

Subsequently, the solvent is separated and reduced in volume. Optionally, the solvent may be extracted with a second solvent. Thereafter, the extraction solvents are collected and reduced in volume either under low pressure or by evaporation to form a residue. Optionally, the residue is diluted and purified by gravity chromatography using at least one suitable solvent easily determined by a skilled artisan with little or no experimentation as the mobile phase. Optionally, the ratio of solvents within the solvent mixture may be gradually changed.

An alternative extraction process comprises adding a suitable solvent to the Magnoliaceae plant body, either grounded into a powder or cut into pieces. The solvents include, but are not limited to water, a lower alcohol, and mixtures thereof. Preferably, the solvents are water, ethanol, or mixtures thereof The mixture of Magnoliaceae plant and solvent is allowed to sit overnight, preferably for about 6 hours to about 40 hours, preferably for about 8 hours to about 18 hours. Subsequently, the mixture is filtered, separating the solids from the filtrate. The solids are mixed with more solvent and allowed to sit overnight, preferably for about 6 hours to about 40 hours, preferably from about 12 hours to 32 hours, and more preferably from about 8 hours to about 18 hours. The mixture is separated a second time by filtration and the filtrates from both extractions are combined, and concentrated under reduced pressure to obtain a residue. The residue is vacuum dried for about 1 to about 10 hours, preferably for about 1 to about 2 hours at room temperature.

Yet another alternative extraction process comprises combining a suitable solvent to the Magnoliaceae plant body, either grounded into a powder or cut into pieces, in a ratio of about 4:1 to about 7:1 by volume to form a mixture. The mixture is heated to a temperature of about 1° F. below the boiling point of the solvent and stirred for about an hour. Preferably, if water is used as a solvent, the temperature is about 212° F. The mixture is filtered and the filtrate is washed with fresh solvent in a volume ratio of about 1:1. Subsequently the filtrate is concentrated under reduced volume and dried in a vacuum oven. In this method, suitable solvents include ethanol, methanol, chlorinated solvents, propanol, 2-propanol, water, denatured industrial grade alcohol such as SDA-35, and mixtures thereof. Preferably, suitable solvents include water, ethanol, SDA-35, and mixtures thereof.

INCORPORATION BY REFERENCE

All of the U.S. patents and U.S. published patent applications cited herein are hereby incorporated by reference.

EQUIVALENTS

Those skilled in the art will recognize, or be able to ascertain using no more than routine experimentation, many equivalents to the specific embodiments of the inventions described herein. Such equivalents are intended to be encompassed by the following claims.

I claim:

1. A formulation comprising virgin salmon oil (VSO), phosphatidylserine, honokiol, and magnolol,
   wherein
   the concentration of VSO in the formulation is from about 40% to about 90% by weight of the formulation; and
   the concentration of phosphatidylserine in the formulation is from about 4% to about 20% by weight of the formulation.

2. The formulation of claim 1, wherein the concentration of PUFA in the VSO is from about 20% to about 40% by weight of VSO.

3. The formulation of claim 1, wherein the concentration of honokiol in the formulation is from about 1% to about 10% by weight of the formulation.

4. The formulation of claim 1, wherein the concentration of magnolol in the formulation is from about 1% to about 10% by weight of the formulation.

5. The formulation of claim 1, wherein the formulation further comprises vitamin A; and the concentration of vitamin A in the formulation is from about 0.01% to about 1% by weight of the formulation.

6. The formulation of claim 1, wherein the formulation further comprises olive oil; and the concentration of olive oil in the formulation is from about 5% to about 15% by weight of the formulation.

7. The formulation of claim 1, wherein the formulation does not comprise olive oil.

8. The formulation of claim 1, wherein the formulation does not comprise lecithin.

9. The formulation of claim 1, wherein less than about 18% of the honokiol or the magnolol present in the formulation at day 0 decomposes upon storage of the formulation at about 54° C. and about 75% relative humidity for a period of 21 d.

10. The formulation of claim 1, in the form of oral dosage form.

11. The formulation of claim 10, wherein the oral dosage form is a soft gel capsule.

12. The formulation of claim 1, wherein the formulation consists essentially of VSO, phosphatidylserine, honokiol, and magnolol.

13. The formulation of claim 1, wherein the VSO comprises astaxanthin.

14. The formulation of claim 1, wherein the concentration of PUFA in the VSO is from about 20% to about 30% by weight of VSO.

15. A method of
   reducing disturbances in falling asleep,
   reducing disturbances in staying asleep,
   reducing abnormal sleep behaviors,
   causing rest or relaxation,
   inducing relaxation without inducing muscle relaxation,
   relieving nervous tension or stress,
   increasing focus or concentration, or
   decreasing anxiety,
   comprising administering to a subject in need thereof an effective amount of a formulation of claim 1.

16. The method of claim 15, wherein the subject is a subject suffering from an attention deficit disorder (ADD).

17. The method of claim 15, wherein the subject is a subject who lacks attention to details; makes careless mistakes; lacks sustained attention; is a poor listener; fails to follow through on tasks; has poor organization; avoids tasks requiring sustained mental effort; loses things; is easily distracted; or is forgetful.

18. The method of claim 15, wherein the subject is a subject suffering from an anxiety disorder.

19. The method of claim 18, wherein the anxiety disorder is a panic disorder with or without agoraphobia; agoraphobia without history of panic disorder; an animal phobia; a social phobia; obsessive-compulsive disorder; post-traumatic stress disorder; acute stress disorder; generalized or substance-induced anxiety disorder; neuroses; convulsions; migraine; depressive or bipolar disorders; psychotic disorders; neurodegeneration arising from cerebral ischemia; attention deficit hyperactivity disorder; Tourette's syndrome; speech disorders; or disorders of circadian rhythm.

20. The method of claim 18, wherein the anxiety disorder a single-episode or recurrent major depressive disorder, dysthymic disorder, bipolar I or bipolar II manic disorders, cyclothymic disorder, or schizophrenia.

* * * * *